United States Patent [19]

Arakawa et al.

[11] Patent Number: 5,025,169
[45] Date of Patent: Jun. 18, 1991

[54] SENSOR IN IC FORMATION

[75] Inventors: Masao Arakawa; Tomizo Terasawa; Masanobu Ogawa; Hironori Kami, all of Kadoma, Japan

[73] Assignee: Matsushita Electric Works, Ltd., Kadoma, Japan

[21] Appl. No.: 423,235

[22] Filed: Oct. 18, 1989

[30] Foreign Application Priority Data

Oct. 21, 1988 [JP] Japan ................. 63-265610

[51] Int. Cl.$^5$ ............................................ G01N 15/06
[52] U.S. Cl. ................................. 250/574; 250/214 R; 340/630
[58] Field of Search ............ 250/214 R, 214 SW, 573, 250/574; 340/628, 630; 356/338, 438

[56] References Cited

U.S. PATENT DOCUMENTS

| | | | |
|---|---|---|---|
| 3,678,511 | 7/1972 | Benedict | 340/630 |
| 4,025,915 | 5/1977 | Enemark | 340/630 |
| 4,225,860 | 9/1980 | Conforti | 340/630 |
| 4,481,506 | 11/1984 | Honma | 250/574 |
| 4,506,161 | 3/1985 | Muggli et al. | 340/630 |
| 4,555,634 | 11/1985 | Muggli et al. | 250/574 |
| 4,654,644 | 3/1987 | Dobrzanski | 250/574 |

Primary Examiner—David C. Nelms
Assistant Examiner—Stephone B. Allen
Attorney, Agent, or Firm—Edward W. Osann, Jr.

[57] ABSTRACT

A sensor in IC formation has a light emitting means, and a light receiving means disposed for receiving a faint pulsed light generated by scattering of light emitted from the light emitting means, in which a switching means capable of short-circuiting between sensor circuit lines is provided for being triggered by a counter means operated in response to an output from the light receiving means, and constituent elements of respective components of the sensor including the said means and capable of being formed in the IC are formed as integrated circuits on a dielectric isolation substrate, whereby electric isolation of the respective elements can be made complete irrespective of light irradiation to realize effective interelement junction and isolation.

10 Claims, 10 Drawing Sheets

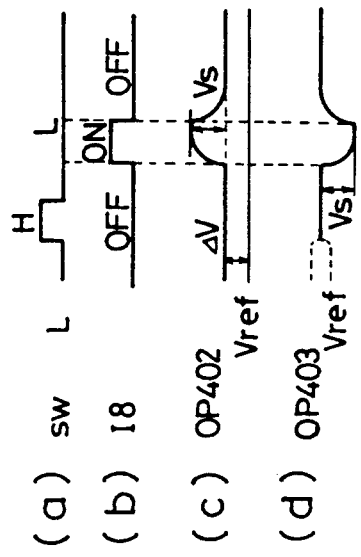
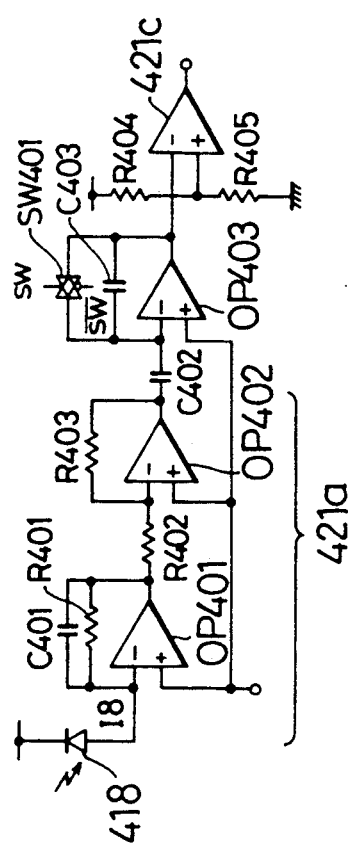
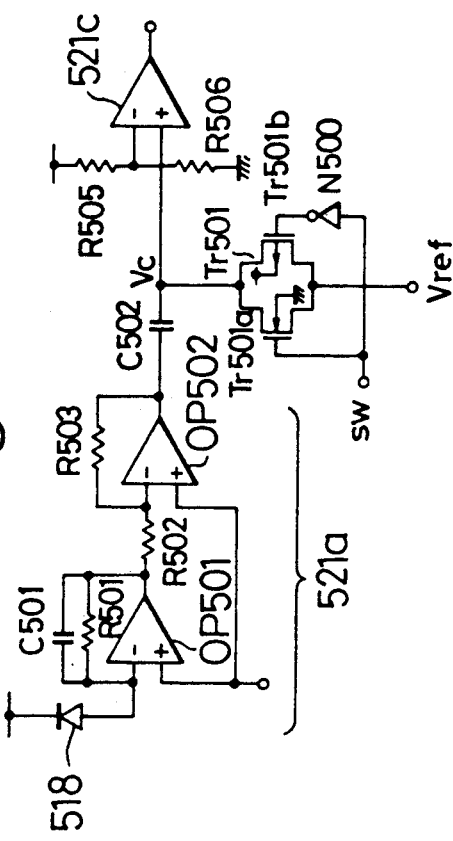

SENSOR IN IC FORMATION

TECHNICAL BACKGROUND OF THE INVENTION

This invention relates to a sensor in IC formation as made into a single chip.

The sensor of the kind referred to can be effectively utilized as a photoelectric smoke sensor or a photoelectric intrusion sensor.

DISCLOSURE OF PRIOR ART

The photoelectric sensor has been widely employed in detecting smoke at initial stage of occurrence of fire or in detecting any intrusion by a person or the like into a detecting area or constructions.

As an example of the known photoelectric sensors, a smoke sensor disclosed in U.S. Pat. No. 4,481,506 of Hiroshi Honma may be enumerated, according to which the sensor includes sensor circuit lines $l_1$ and $l_2$ connected to a receiver, and a direct current voltage is applied across these lines $l_1$ and $l_2$ so that, when these lines are short-circuited, inherent increase in circuit current will be detected to generate an alarm signal. More specifically, the sensor of this patent is provided with a diode bridge which achieves a normal operation even when the lines $l_1$ and $l_2$ are connected in reverse polarity, and a switching circuit is provided at next stage of the diode bridge so as to be turned ON for short-circuiting the lines $l_1$ and $l_2$ by a trigger signal from a count circuit of a post stage.

Further, a constant voltage circuit is connected to the lines $l_1$ and $l_2$ for converting the direct current voltage obtained at a DC output terminal of the diode bridge into a predetermined constant voltage, which voltage is applied to predetermined internal circuits. At next stage of the constant voltage circuit, an oscillating circuit is connected so that a reference clock signal will be provided from this oscillating circuit to a timing control circuit where the reference clock signal is frequency-divided to provide to a driving circuit for a post-stage light emitting element a light-emission control signal for controlling light-emission timing of the light emitting element which is thereby driven intermittently.

A light receiving element is disposed for receiving a faint pulsed light generated as an emitted pulsed light from the light emitting element is scattered by smoke particles, and an output signal provided from the light receiving element in response to the received pulsed light is amplified through an amplifier to be a first input to a post-staged comparator. At this moment, a reference signal is provided as a second input to the comparator from a reference voltage source, the first and second inputs are compared with each other, and it is thus discriminated whether or not the output signal from the light receiving element is at a scattering level due to the smoke. In this case, the comparator is connected to a count circuit which turns ON a switch circuit so that, when the comparator provides its output signal to the count circuit more than twice, for example, the count circuit will provide to the switch circuit a trigger signal.

In order to fabricate such relatively large scale sensor circuit as shown in the foregoing U.S. patent into a sensor minimized in size and weight and made also inexpensive, the circuit will be generally formed into a semiconductor integrated circuit employing PN junction and isolation to form therein CMOS, DMOS and bipolar elements which are electrically isolated from one another by a reverse bias applied to the PN junction. While this circuit employing the PN junction and isolation is simpler and inexpensive, there remains a problem that the electrical isolation of the elements is incomplete when light is caused to be incident upon the PN junction, and it is another problem that a leak current between the respective elements is likely to become relatively large to render an interelement coupling to be difficult to avoid.

TECHNICAL FIELD

A primary object of the present invention is, therefore, to provide a sensor in the IC formation which allows a complete isolation to be achieved between respective constituent elements irrespective of the incident light even in a relatively large scale photoelectric sensor arrangement involving a variety of the elements high and low in the withstand voltage, and is capable of remarkably reducing the occurrence of malfunction due to any interference between the elements by restraining leak current between them and lowering as far as possible the probability of causing any false alarming or of failing to give any alarming.

According to the present invention, the above object is attained by a sensor in an IC formation wherein sensor circuit lines are connected to a switching means for short-circuiting between the lines and a power source means for taking out from the lines a source voltage, the power source means is connected at its post stage to an intermittent operating means, light emitting means and driving means for the light emitting means, the intermittent operating means being arranged for driving the driving means to intermittently actuate the light emitting means, a light receiving means is provided for receiving a faint pulsed light generated as light from the light emitting means is scattered, and a comparing means is provided to receive an amplified signal of an output from the light receiving means together with a reference signal, an output of the comparing means being provided to a counter means for providing a trigger signal to the switching means, characterized in that the respective means are formed into integrated circuits of constituent elements on a dielectric isolation substrate.

Other objects and advantages of the present invention shall be made clear in following explanation of embodiments of the invention.

BRIEF EXPLANATION OF DRAWINGS

FIG. 17 is a circuit diagram showing a light receiving and signal processing circuit in another working aspect and employable in the sensor of FIG. 1;

FIG. 18 shows operational waveforms in the circuit of FIG. 17;

FIG. 19 is a circuit diagram showing the light receiving element and signal processing circuit in still another working aspect employable in the sensor of FIG. 1;

Figure 1:
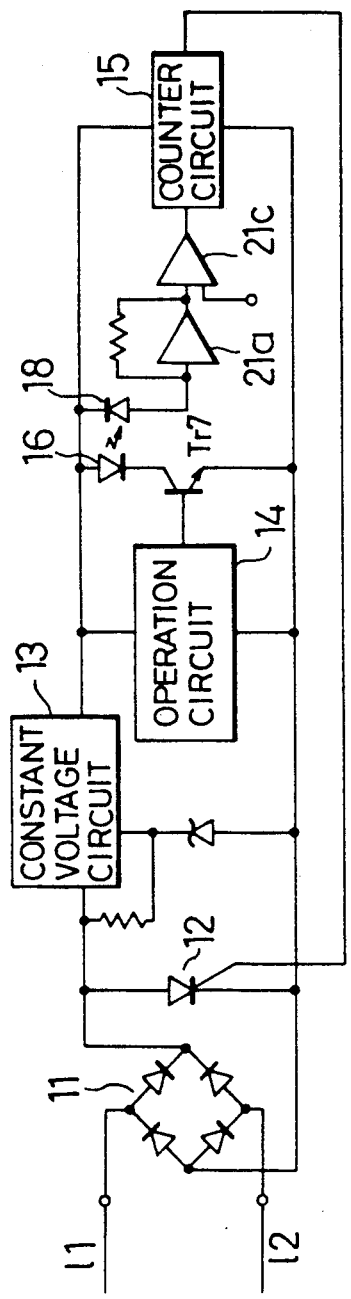
FIG. 1 is a block diagram of a sensor in IC formation according to the present invention.

While the present invention shall now be detailed in the followings with reference to the embodiments shown in the drawings, it should be appreciated that the intention is not to limit the invention only to these embodiments but rather to include all modifications, alterations and equivalent arrangements possible within the scope of appended claims.

DISCLOSURE OF PREFERRED EMBODIMENTS

Figure 2:
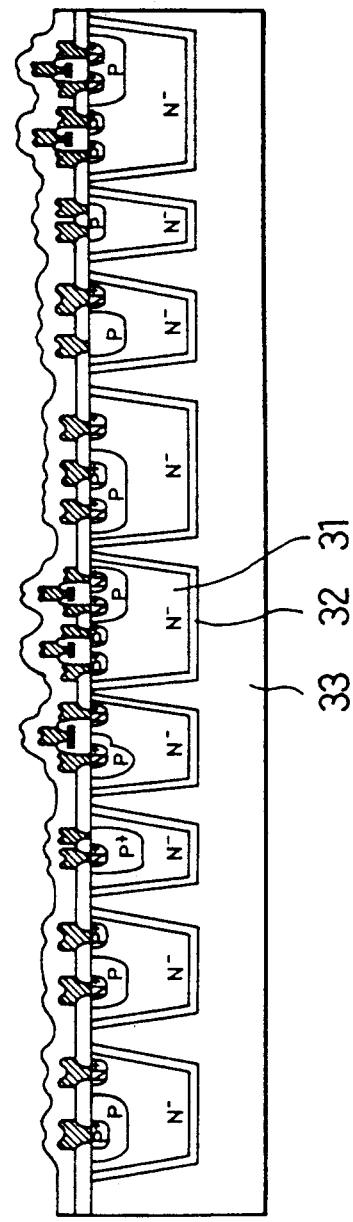
FIG. 2 is a sectioned view of a dielectric isolation type integrated circuit which realizing the sensor shown in FIG. 1.
Figure 3:
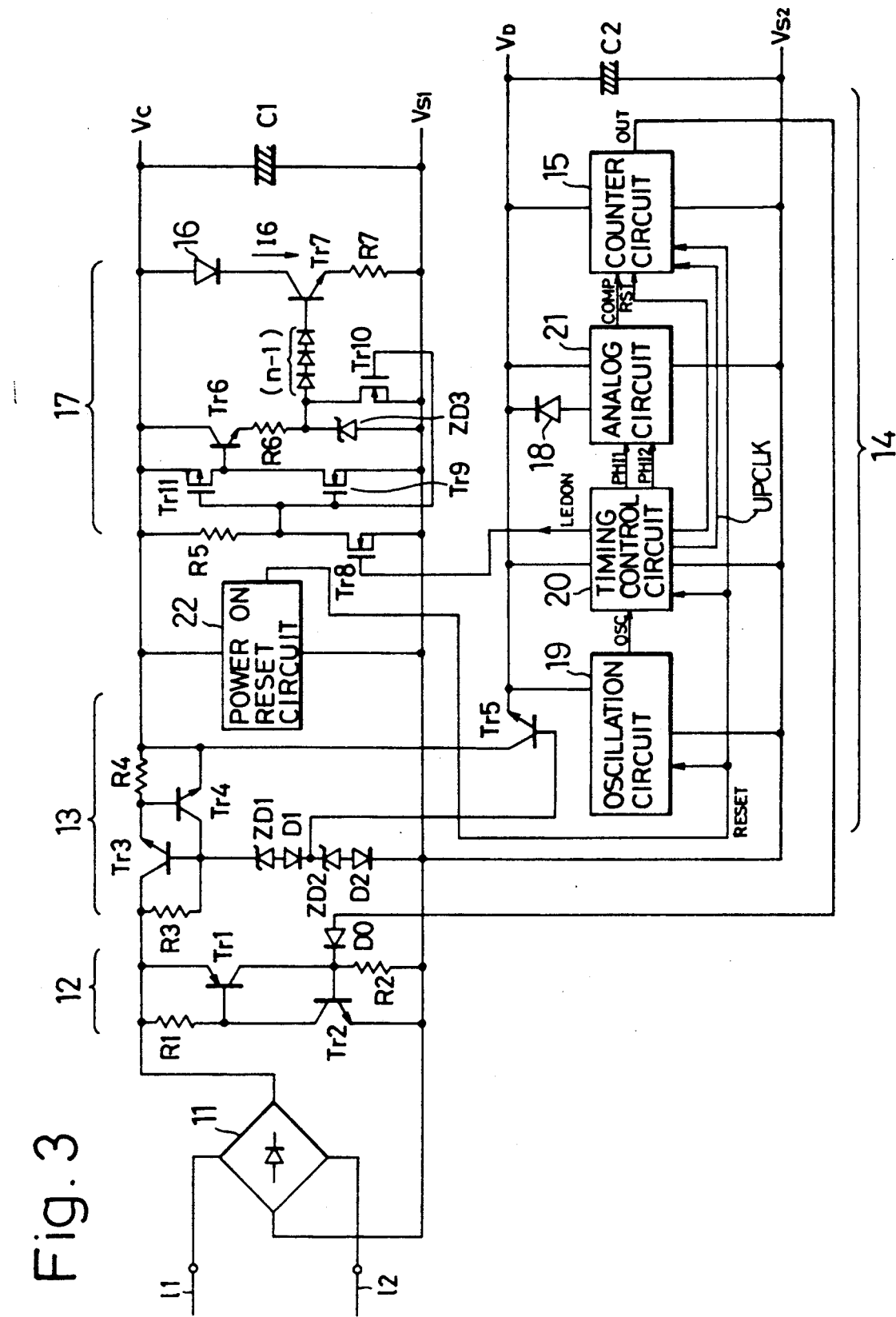
FIG. 3 is a more detailed circuit diagram of the sensor of FIG. 1.

Referring now to FIGS. 1 to 3, a sensor according to the present invention includes sensor circuit lines 11 and 12 connected to a signal receiving means (not shown) and a diode bridge 11 connected to the lines 11 and 12 for being operatable even when the connection of the lines 11 and 12 to the signal receiving means is reversed. With respect to the sensor circuit lines 11 and 12, further, there are connected sequentially a switching circuit 12, a constant voltage circuit 13 and an operation circuit 14.

The switching circuit 12 may be either such thyristor as in FIG. 1 or such combination of PNP transistor Tr1 and NPN transistor Tr2 as in FIG. 3 which are forming a self-maintaining circuit. In the latter case, the PNP transistor Tr1 is connected at its emitter to a positive output terminal of the diode bridge 11, while the NPN transistor Tr2 is connected at its emitter to a negative output terminal of the diode bridge 11. The base of the PNP transistor Tr1 is connected to the collector of the NPN transistor Tr2 while the base of the NPN transistor Tr2 is connected to the collector of the PNP transistor Tr1, and resistors R1 and R2 are inserted respectively between the base and the emitter of the transistors Tr1 and Tr2. In this case, the base of the NPN transistor Tr2 forms a trigger terminal of the switching circuit 12, which terminal being connected to an output terminal of a later detailed counter circuit 15. When this counter circuit 15 provides an H level output, therefore, a base current is made to flow through a diode D0 to the NPN transistor Tr2, an eventual collector current of this transistor causes a base current to flow to the PNP transistor Tr1, an eventual collector current of this PNP transistor Tr1 causes the base current of the NPN transistor Tr2 to flow, and the switching circuit 12 comes to a self-maintaining state.

Here, the DC output terminals of the diode bridge 11 are short-circuited through the switching circuit 12 and eventually a short-circuit takes place across the circuit lines 11 and 12, due to which a circuit current flowing between the lines 11 and 12 increases, and an output current is detected by the receiver connected to the other ends of the lines 11 and 12. This state causes a reset switch provided on the side of the receiver to be actuated to have the state maintained until the circuit current flowing through the circuit lines 11 and 12 is interrupted.

The constant voltage circuit 13 comprises three NPN transistors Tr3, Tr4 and Tr5, in which the transistor Tr3 is connected at the collector to the positive output terminal of the diode bridge 11, and at the base to the negative output terminal of the diode bridge 11 through a first constant voltage element comprising a series circuit of a Zener diode ZD1 and a diode D1 and a second constant voltage element comprising a series circuit of a Zener diode ZD2 and a diode D2. The diodes D1 and D2 are provided for compensating for the temperature coefficient of Zener voltage of the Zener diodes ZD1 and ZD2. To the first and second constant voltage elements, a current from the positive output terminal of the diode bridge 11 is made to flow, through a biasing resistor R3 connected between the collector and the base of the transistor Tr3, whereby a constant voltage $V_{ZD1}+V_F$ which is the sum of a Zener voltage $V_{ZD1}$ of the Zener diode ZD1 and a normal directional fall voltage $V_F$ of the diode D1 is generated across the first constant voltage element. Across the second constant voltage element, on the other hand, a constant voltage $V_{ZD2}+V_F$ which is the sum of a Zener voltage $V_{ZD2}$ of the Zener diode ZD2 and a normal directional fall voltage $V_F$ of the diode D2 is generated.

At the base of the transistor Tr3, therefore, there is generated a voltage $V_{ZD1}+V_{ZD2}+2V_F$ which is the sum total of the both voltages across the first and second constant voltage elements. Assuming here that a voltage across the base and emitter of the transistor Tr3 is $V_{BE3}$, an emitter voltage of the transistor Tr3 is $V_{ZD1}+V_{ZD2}+2V_F-V_{BE3}$, which is made constant, and this voltage is charged in a power source capacitor C1 through a resistor R4 of a low resistance, so as to be a source voltage across power source lines Vc and Vs1. The transistor Tr4 is provided for excess current prevention and, as the voltage appearing across the low resistor R4 is small so long as the emitter current of the transistor Tr3 is of a proper level, the transistor Tr4 does not operate. When the emitter current of the transistor Tr3 increases abnormally, a voltage appearing across the resistor R4 causes a base current to flow to the base of the transistor Tr4, the base current of the transistor Tr3 is shunted through the collector and emitter of the transistor Tr4, and the emitter current of the transistor Tr3 is controlled.

Assuming on the other hand that a voltage across the base and emitter of the transistor Tr5 is $V_{BE5}$, the emitter voltage of the transistor Tr5 will be constant at $V_{ZD2}+V_F-V_{BE5}$, and this voltage is charged to a power source capacitor C2, so as to be a source voltage across power source lines Vd and Vs2.

The operation circuit 14 includes a light emitting element 16, driving circuit 17, light receiving element 18, oscillation circuit 19, timing control circuit 20, analog signal processing circuit 21 and the counter circuit 15 which provides the trigger output as in the above, and a power-on reset circuit 22 is inserted between the constant voltage circuit 13 and the driving circuit 17.

The driving circuit 17 includes two NPN transistors Tr6 and Tr7, three NMOS transistors Tr8, Tr9 and Tr10 and one PMOS transistor Tr11, which are so arranged that, when a light emission control signal LEDON from the timing control circuit 20 is at H level, a driving current I6 will be provided to the light emitting element 16 but, when the signal LEDON is at L level, the current will not be fed to the element 16 and the driving circuit 17 itself is additionally made to be in a high impedance state of consuming no power. The delight emission control signal LEDON from the timing control circuit 20 is being applied to the gate of the NMOS transistor Tr8, so that the source of this NMOS transistor Tr8 will be connected to the source line Vs1 while the drain will be connected to the source line Vc through a biasing resistor R5. A junction point of the resistor R5 and NMOS transistor Tr6 is connected to the gates of the NMOS transistors Tr9 and Tr10 and of the PMOS transistor Tr11, while the NMOS transistors Tr9 and Tr10 are connected at their sources to the source line Vs1 and the PMOS transistor Tr11 is connected at the source to the source line Vc. The NMOS transistor Tr9 and PMOS transistor Tr11 are connected at their drains commonly to the base of the NPN transistor Tr6 which is connected at the collector to the source line Vc and at the emitter through a resistor R6 to the cathode of a Zener diode ZD3 the anode of which is connected to the source line Vs1.

To the cathode of the Zener diode ZD3, the drain of the NMOS transistor Tr10 is connected, and the base of the NPN transistor Tr7 is also connected through a series connected array of (n−1) diodes while this transistor Tr7 is also connected at the emitter through a resistor R7 to the source line Vs1. Further, the collector of this NPN transistor Tr7 is connected to the cathode of the light emitting element 16 which is connected at the anode to the source line Vc.

When the light emission control signal LEDON from the timing control circuit 20 is made at H level in the driving circuit 17, therefore, the NMOS transistor Tr8 is turned ON to render the gate potential of the NMOS transistors Tr9 and Tr10 and of the PMOS transistor Tr11 to be lowered, so that the NMOS transistors Tr9 and Tr10 will be made in OFF state whereas the PMOS transistor Tr11 will be turned ON. Due to this, the base potential of the NPN transistor Tr6 is raised to cause a current to flow, through the collector and emitter of the NPN transistor Tr6, to a series circuit of the resistor R6 and Zener diode ZD3, whereby a voltage is generated at the cathode of the Zener diode ZD3, the voltage being equal to its Zener voltage $V_{ZD3}$. A voltage which is a balance of the thus generated voltage from which the normal directional voltage fall $(n-1) \times V_F$ at the series array of the (n−1) diodes is deducted is applied to the base of the NPN transistor Tr7 to turn it ON, and the driving current I6 is made to flow to the light emitting element 16.

When the light emission control signal LEDON from the timing control circuit 20 is at L level, the NMOS transistor Tr8 is made into OFF state, the gate potential of the NMOS transistors Tr9 and Tr10 and PMOS transistor Tr11 is raised by the biasing resistor R5 to turn the NMOS transistors Tr9 and Tr10 to be in ON state while PMOS transistor Tr11 is thereby turned to be in OFF state, due to which the base potential of the NPN transistor Tr6 falls so that no current will flow through the collector and emitter of the NPN transistor Tr6. As a short-circuited state is attained across the Zener diode ZD3 through the NMOS transistor Tr10, the cathode potential of the Zener diode ZD3 is lowered, so that the NPN transistor Tr7 will be in OFF state and no driving current I6 will flow through the light emitting element 16.

The power-on reset circuit 22 detects voltage rise in the power source capacity C1 and provides a power-on reset signal RESET to the oscillation circuit 19, timing control circuit 20 and counter circuit 15. The analog signal processing circuit 21 comprises, as will be detailed later, an amplifier, comparator and reference voltage circuit, and is directly connected to the light receiving element 18.

In the present instance, a reference clock signal OSC is fed from the oscillation circuit 19 to the timing control circuit 20 where the reference clock signal OSC is frequency divided, and the timing control circuit 20 provides timing control signals PHI1 and PHI2 to the analog signal processing circuit 21, in addition to the supply of the light emission control signal LEDON to the driving circuit 17, and also provides a reset signal RST and an up-clock signal UPCLK to the counter circuit 15. From the analog signal processing circuit 21, a comparison output signal COMP is supplied to the counter circuit 15. These oscillation circuit 19, timing control circuit 20, analog signal processing circuit 21 and counter circuit 15 are capable of being operated at a low voltage and consume less current, and they receive a source power from the capacitor C2. On the other hand, the driving circuit 17 for the light emitting element 16 consumes a large current instantaneously and is made to receive the power from the other capacitor C1 than the capacitor C2. By separating in this manner the source line for the driving circuit 17 from the source line Vd for other circuits, it is made possible to prevent the source voltage for such other circuits from being lowered in a moment upon the light emission of the light emitting element 16, and thus to prevent any malfunction from occurring at the other circuits.

Figure 4:
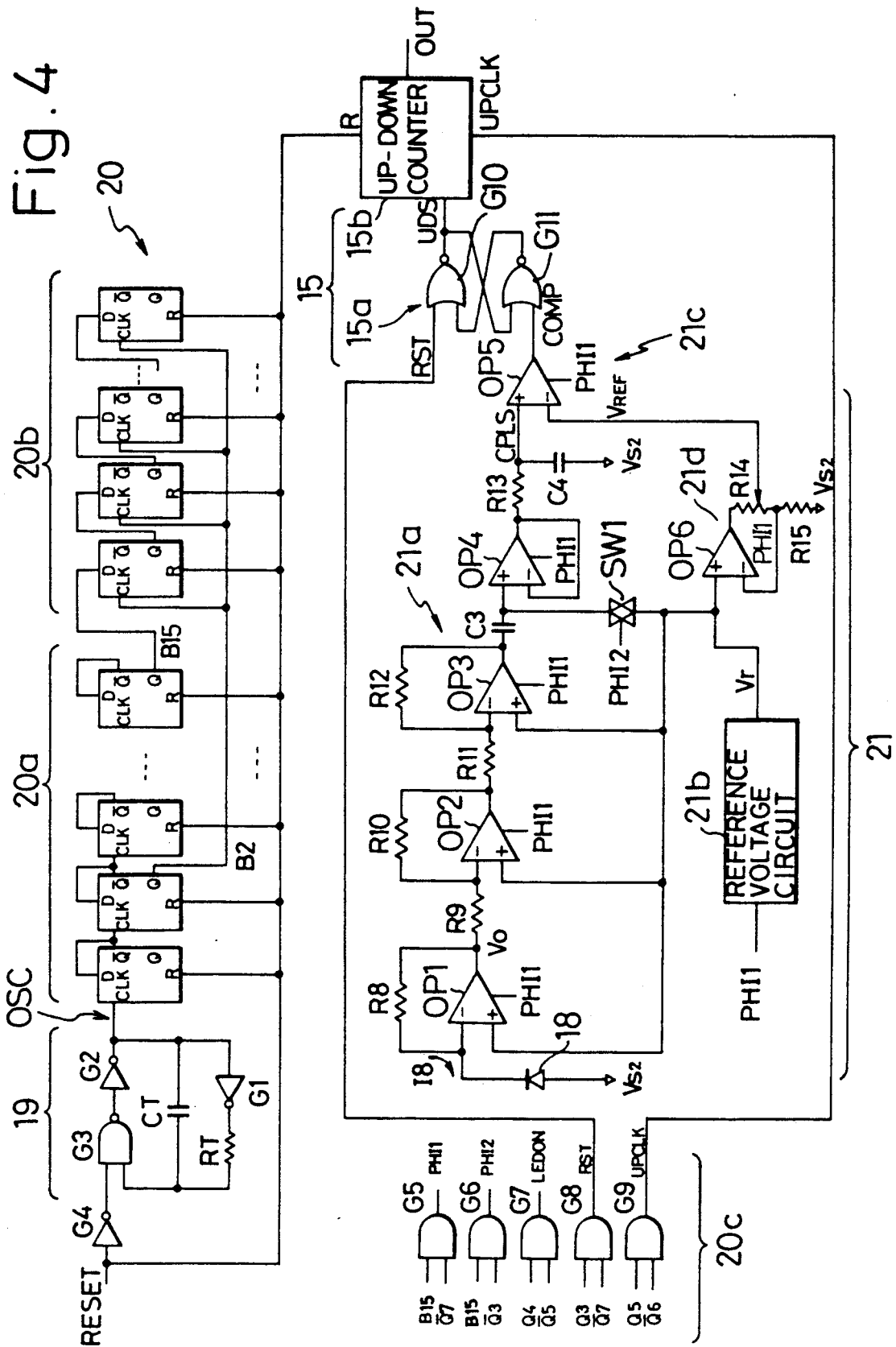
FIG. 4 is a detailed circuit diagram showing an oscillating circuit and a timing control circuit in the sensor of FIG. 1.

Referring also to FIG. 4, the oscillation circuit 19 comprises in the concrete a capacitor CT and resistor RT for setting a time constant, two inverters G1 and G2, and an oscillation controlling NAND gate G3. One input terminal of this NAND gate G3 is connected through the resistor RT to an output terminal of the inverter G1, an through the capacitor CT to an input terminal of the inverter G1 and output terminal of the inverter G2, while an output terminal of the NAND gate G3 is connected to an input terminal of the inverter G2 and the power-on reset signal RESET is provided through an inverter G4 to the other input terminal of the NAND gate G3. When the power-on reset signal RESET is at L level, an output of the inverter G4 will be on H level to have the NAND gate G3 turned to be in a state for passing therethrough any signal, a reference clock signal OSC of a cycle determined by a time constant of the resistor RT and capacitor CT is provided out of the output terminal of the inverter G2.

This reference clock signal OSC is provided to a frequency divider 20a in the timing control circuit 20. The frequency divider 20a itself is formed preferably by means of a cascade connection in 15 stages of D flip-flops respectively having an inverted output terminal $\overline{Q}$ connected to its own data input terminal D and also to a clock input terminal CLK of adjacent flip-flop at next stage. The reference clock signal OSC is received at a clock input terminal of the D flip-flop at first stage, and a frequency divided output B15 of the reference clock signal OSC is obtained at an output terminal Q of the last stage D flip-flop. This frequency divided output B15 is provided to a seven stage shift register 20b also in the timing control circuit 20, the shift register 20b also comprising a 7 stage cascade connection of the D flip-flops respectively having an output terminal Q connected to the data input terminal D of the next stage D flip-flop. To the data input terminal D of the first stage D flip-flop, the frequency divided output B15 is provided, while the respective stage D flip-flops receive at their clock input terminal CLK a frequency divided output B2 from the output terminal Q of the second stage D flip-flop in the frequency divider 20a. To reset input terminals R of the respective D flip-flops of both of the frequency divider 20a and shift register 20b, the power-on reset signal RESET is being supplied Outputs from the output terminals Q3, $\overline{Q3}$, Q4, Q5, $\overline{Q5}$, Q6 and $\overline{Q7}$ of the third to seventh stage D flip-flops in the shift register 20b as well as the frequency divided output B15 of the frequency divider 20a are provided to AND gates G5 through G9 forming a logical circuit 20c in the timing control circuit 20, so as to prepare respective control signals PHI1, PHI2, LEDON, RST and UPCLK.

The analog signal processing circuit 21 includes an amplifying means 21a which comprises three stage cascade connection of operational amplifiers OP1, OP2 and OP3, to non-inverted input terminals of which a reference voltage Vr is applied from a reference voltage circuit 21b. To an inverted input terminal of the first stage operational amplifier OP1, a silicon photodiode SPD forming the light receiving element 18 is connected at its cathode, while the anode of the element 18 is connected to the power source line Vs2 so that PN junction in the element 18 will be reverse biased, and a photoelectric current caused to flow through the PN junction in reverse direction due to a light irradiation is detected by the operational amplifier OP1 as a voltage signal. To this end, a feedback resistor R8 connected between an output terminal and the inverted input terminal of the first stage operational amplifier OP1 is made to be of a high resistance value. For the second operational amplifier OP2, a voltage amplification circuit is employed, the voltage amplification factor of which is determined by a ratio of an input resistor R9 and a feedback resistor R10. An output terminal of the third stage operational amplifier OP3 is connected to an end of a direct-current cutting capacitor C3 the other end of which is connected to a non-inverted input terminal of a further operational amplifier OP4. An output terminal of this operational amplifier OP4 is fed back to its own inverted input terminal, and is thus regarded as a buffer amplifier operating as an impedance converter.

The output terminal of the operational amplifier OP4 is also connected through a low pass filter comprising a resistor R13 and a capacitor C4 to a non-inverted input terminal of an operational amplifier OP5 employed as a comparator. The direct-current cutting capacitor C3 is connected also at the other end through an analog switch SW1 to an output terminal of the reference voltage circuit 21b, and an output of this circuit 21b is provided also to a non-inverted input terminal of a further operational amplifier OP6 which is connected at its output terminal through resistors R14 and R15 to the power source line Vs2, and these resistors R14 and R15 are connected at their junction point to an inverted input terminal of the operational amplifier OP6. Here, a reference voltage $V_{REF}$ obtained at the resistor R14 is being provided to an inverted input terminal of the operational amplifier OP5 as the comparator, and an output of this operational amplifier OP5 is employed as a SET input to RS flip-flop 15a comprising NOR gates G10 and G11 which forming part of the counter circuit 15. As a RESET input to this RS flip-flop 15a, a reset signal RST from the AND gate G8 is employed, and an output of the RS flip-flop 15a is made as an up-down selection signal UDS for an up-down counter 15b in the counter circuit 15. To a reset input terminal of the up-down counter 15b, the power-on reset signal RESET is supplied, while an up-clock signal UPCLK provided out of the AND gate G9 is provided to an up-clock input terminal UPCLK.

Figure 5:
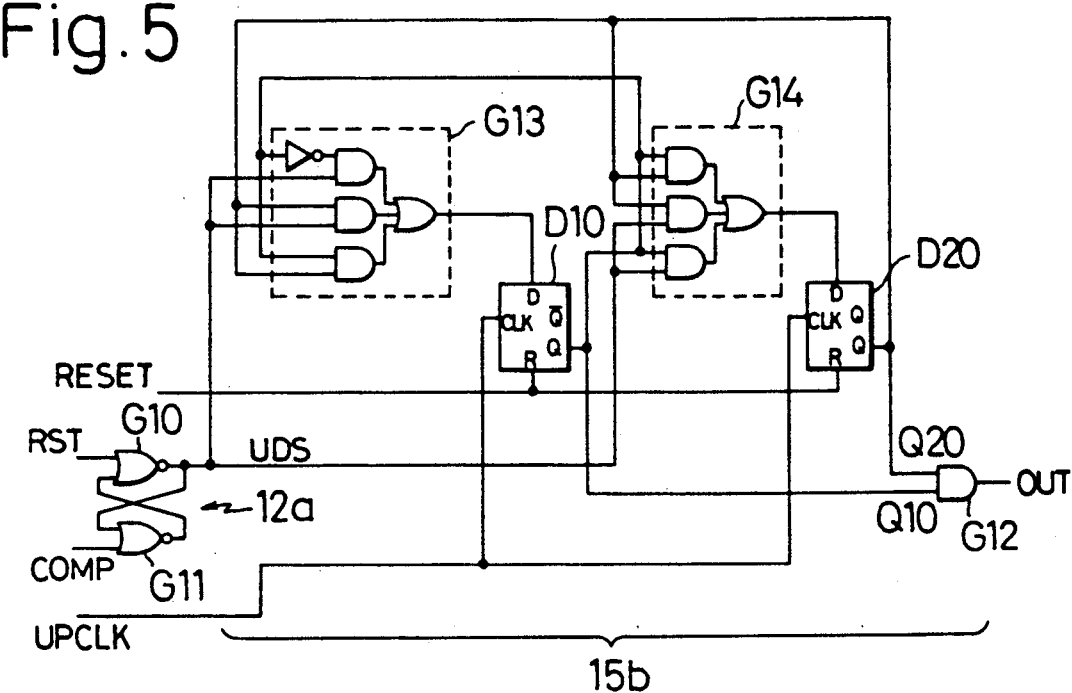
FIG. 5 is a detailed circuit diagram showing a counter circuit in the sensor of FIG. 1.

Referring also to FIG. 5, the up-down counter 15b comprises in the concrete two D flip-flops D10 and D20, the power-on reset signal RESET is supplied to reset input terminals R of the respective flip-flops, and the up-clock signal UPCLK is provided to their clock input terminals CLK. Outputs of these flip-flops D10 and D20 are provided to an AND gate G12, and an output of this AND gate G12 is made to be an output signal OUT of the counter circuit 15. Data input terminals D of the both flip-flops D10 and D20 are to receive singals generated by logical circuits G13 and G14 on the basis of the up-down selection signal UDS and output signals from output terminals Q of the both flip-flops. In the present instance, the output signal OUT is made to be at H level when three sequential presence at H level of the comparison output signal COMP, and the switching circuit 12 is thereby triggered.

In the driving circuit 17, on the other hand, the driving current for the light emitting element 16 will be, with the Zener voltage of the Zener diode ZD3 assumed to be $V_{ZD3}$, $$I6 = \{V_{ZD3} - (n-1) \times V_F - V_{BE7}\}/R7 = (V_{ZD3} - n \times V_F)/R7$$

wherein the voltage $V_{BE7}$ across the base and emitter of the transistor Tr7 is assumed to be equal to the normal directional fall voltage $V_F$ of each of the (n−1) diodes. In the driving circuit 17, as will be clear from the above, the temperature characteristics of the voltage $V_{BE7}$ across the base and emitter of the transistor Tr7 are to give influence on the temperature characteristics of the driving current I6 for the light emitting element 16.

Figure 6:
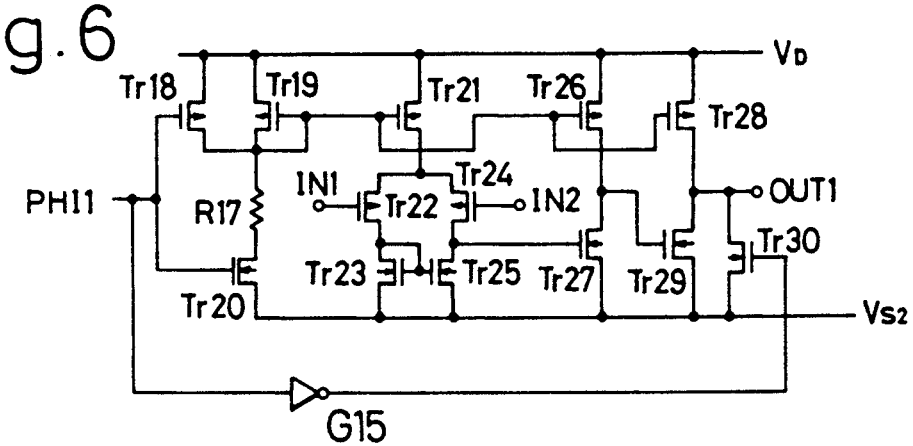
FIG. 6 is a detailed circuit diagram showing an operational amplifier in the timing control circuit in the sensor of FIG. 1.

Referring to FIG. 6, the operational amplifiers OP1 to OP6 of the analog signal processing circuit 21 comprise, in the concrete, MOS transistors Tr18 through Tr30, resistor R17 and inverter G15, which are arranged so that, when the control signal PHI1 is at H level, an amplified voltage signal of a differential voltage at both input terminals IN1 and IN2 is generated at an output terminal OUT1 and, when the control signal PHI1 is at L level, the output terminal OUT1 is made to be at L level so as not to cause any current to flow across the power source lines Vd and Vs2. More specifically, the control signal PHI1 at H level causes the gate potential of the PMOS transistor Tr18 and NMOS transistor Tr20 to be raised, so that the PMOS transistor Tr18 will be in OFF state whereas the NMOS transistor Tr20 will be in ON state. The other PMOS transistors Tr19, Tr21, Tr26 and Tr28 are made to lower the gate potential and are caused to act as resistive elements. Due to this, a voltage corresponding to a difference of the voltages applied to the both input terminals IN1 and IN2 is prepared by a differential amplifier formed by the MOS transistors Tr22 to Tr25, and this voltage is amplified through two stages of the MOS transistors Tr27 and Tr29 and provided at the output terminal OUT1, upon which the MOS transistors Tr26 and Tr28 are to operate as a load resistance of the MOS transistors Tr27 and Tr29. As the control signal PHI1 is at L level, the gate voltage is lowered at the PMOS transistor Tr18 and NMOS transistor Tr20, so that the PMOS transistor Tr18 is made ON state while the NMOS transistor Tr20 is made to be OFF state. Accordingly, the PMOS transistors Tr19, Tr21, Tr26 and Tr28 raise their gate potential and turn into breaking state, so that no current will be made to flow from the power source line Vd to the other power source line Vs2. The inverter G15 is receiving the power from the both lines Vd and Vs2 but, as the inverters in the present embodiment are all consisting of CMOS inverter, no current will flow therethrough after the state transition took place. In the L level state of the control signal PHI1, therefore, the operational amplifiers OP1 to OP6 never consume any electric power at all.

Figure 7:
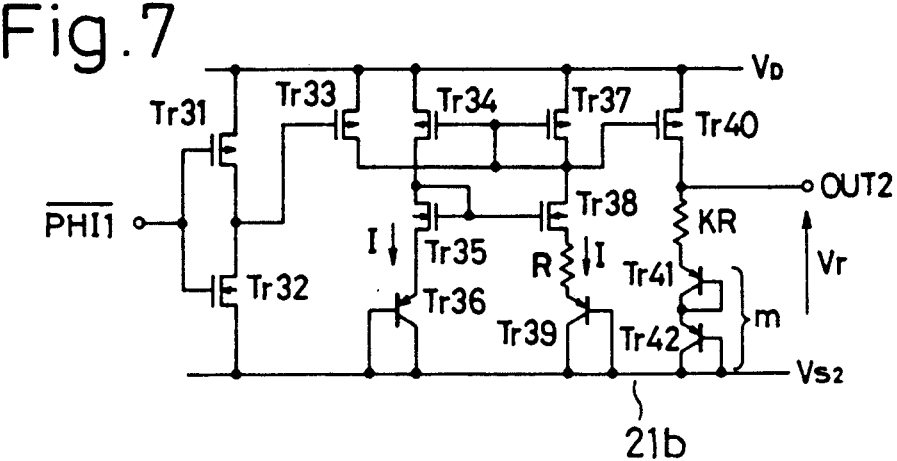
FIG. 7 is a detailed circuit diagram showing a reference power source circuit in the sensor of FIG. 1.

Referring now to FIG. 7, the reference voltage circuit 21b, in the concrete, generates the reference voltage Vr at its output terminal OUT2 when an inverted signal $\overline{PHI1}$ of the control signal $\overline{PHI1}$ is at L level and, when this inverted signal PHI1 is at H level, operates to have the current from the power source line Vd to the power source line Vs2 to be interrupted. More specifically, assuming that the voltage across the base and emitter of the transistors Tr36 and Tr39 are $V_{BE36}$ and $V_{BE39}$ and the current flowing through the transistors Tr36 and Tr39 is I, $$V_{BE36} = V_{BE39} + I \cdot R \quad (1)$$

If the ratio of the emitter surface areas of the both transistors Tr36 and Tr39 is selected to be 1:S, their collector currents $I_{C36}$ and $I_{C39}$ will be $$I_{C36} = I_s \cdot exp(V_{BE36}/V_T), \quad I_{C39} = S \cdot I_s \cdot exp(V_{BE39}/V_T)$$

wherein Is is suturated current, $V_T = kT/q \cdot k$ is the Boltzmann's factor, q is an electron charge, and T is absolute temperature.

Substituting the above formula (1) by these equations, $$I = (V_T/R) \ln S$$

and, assuming that the number of the transistors Tr41, Tr42 ... is m, $$V_0 = I \cdot KR + mV_{BE} = mV_{BE} + (V_T/R) \ln S$$

When the temperature characteristics are to be made zero, $$\partial V_0/\partial T = m \cdot \partial V_{BE}/\partial T + k \cdot \ln S \cdot \partial V_T/\partial T = 0$$

Selecting here that m = 2 and S = 2, then, $$\partial V_{BE}/\partial T = -2mV/°C.$$

$$\partial V_T/\partial T = 0.085 mV/°C.$$

and k = 67.89.

When R = 1 kΩ, then KR will be 67.9 kΩ, and will be a constant voltage circuit of temperature coefficient 0. With m and s optimumly selected, the output voltage Vr can be maintained constant.

In the present embodiment, an optical detecting circuit the received-light output Vo of which does not fluctuate with respect to the temperature is to be realized by regulating the temperature characteristics of the driving current I6 for the driving circuit 17 on the basis of the temperature coefficient of the light emitting and receiving elements 16 and 18, resistor R8 of high resistance value for the current-voltage conversion and output voltage Vr of the reference voltage circuit 21b.

A received-light output current $I_{18}$ is made to flow to the high resistor R8 of first stage operational amplifier OP1 and converted into a voltage signal. When an output voltage of the reference voltage circuit 21b is made to be Vr, then the output voltage Vo of the operational amplifier OP1 will be $$Vo = Vr - I8 \cdot R8$$

When the partial differential coefficient with respect to a variation $\partial T$ in the temperature T on both sides of this equation is obtained, the same will be $$\partial Vo/\partial T = \partial Vr/\partial T - (I8 \cdot \partial R8/\partial T + R8 \cdot \partial I8/\partial T)$$

When the equation is modified so that $\partial Vr/\partial T = 0$, it will be $$\partial Vo/\partial T = -(I8 \cdot \partial R8/\partial T + R8 \cdot \partial I8/\partial T)$$
$$= -I8 \cdot R8\{1/R8 \cdot (\partial R8/\partial T) + 1/I8 \cdot (\partial I8/\partial T)\}$$

Assuming here that the high value resistor R8 for the current-voltage conversion comprises a diffusion resistor of an integrated circuit, that its temperature fluctuation component $\{(1/R8) \cdot (\partial R8/\partial T)\}$ is 2,000 ppm/°C., and further that the temperature fluctuation component $\{(1/I8) \cdot (\partial R8/\partial T)\}$ of the received-light output voltage I8 at the light receiving element 18 is −2,000 ppm/°C., then the partial differential coefficient will be $$\partial Vo/\partial T = -I8 \cdot R8 \cdot 0 ppm/°C. = 0v/°C.$$

However, so long as the light receiving element 18 is an ordinary silicon photodiode (SPD), the temperature coefficient of the received-light output current I8 is positive, and it is impossible to render the temperature fluctuation of the output voltage Vo to be zero. For rendering the fluctuation to be zero, it will be sufficient to have the emitted light amount of the light emitting element 16 reduced as the temperature rises so that the temperature fluctuation component of the received-light output current I8 of the light receiving element 18 will have a negative gradient. That is, as it is considered that the received-light output current I8 of the light receiving element 18 is proportional to the emitted light amount of the light emitting element 16 while this emitted light amount of the element 16 is proportional to the driving current I6, it becomes only necessary to have the emitted light amount of the light emitting element 16 reduced in accordance with the temperature rise. It should be appreciated here that, when the temperature coefficient of the received light output current of the light receiving element 18 alone is assumed to be 3,000 ppm/°C., the temperature coefficient ($\partial Vo/\partial T$) substantially can approximate zero by rendering the temperature coefficient of the emitted light amount of the light emitting element 16 to be $-5,000$ ppm/°C.

Referring further to the temperature characteristics of the driving circuit 17, it should be assumed here that the Zener voltage of the Zener diode ZD3 is $V_{ZD3}$ in FIG. 3, and that the voltage across the base and emitter of the transistor Tr7 as well as the normal directional falling voltage at each of the series array of (n−1) diodes are $V_F$, the current flowing to the light emitting element 16 will be $$I6 = \{V_{ZD3} - n \cdot V_F\}/R7$$

When the partial differential coefficient is obtained with respect to the variation $\partial T$ in the temperature T on both sides of the equation, it will be $$\begin{aligned}\partial I6/\partial T &= 1/R7 \cdot (\partial V_{ZD3}/\partial T) - 1/R7 \cdot (\partial R7/\partial T) \cdot V_{ZD3} - \\ &\quad n/R7 \cdot (\partial V_F/\partial T) + 1/R7 \cdot (\partial R7/\partial T) \cdot n \cdot V_F \\ &= I6 \left[\{1/(V_{ZD3} - n \cdot V_F)\} \cdot \{(\partial V_{ZD3}/\partial T) - \right. \\ &\quad \left. n \cdot (\partial V_F/\partial T)\} - (\partial R7/\partial T)\right]\end{aligned} \quad (2)$$

When the temperature fluctuation of the light emission efficiency of the light emitting element 16 is assumed to be $-6,250$ ppm/°C., the emitted light amount of the light emitting element 16 fluctuates by $+25\%$ to $-25\%$ in a temperature range of $-15°$ to $65°$ C. The emitted light amount of the light emitting element 16 decreases as the temperature rises and, even if the received light output current I8 of the light receiving element 18 is decreased, the emitted light output current of the light receiving element 18 alone as well as the high resistance value of the resistor R8 for the current-voltage conversion show a tendency of being increased as the temperature rises. If the emitted light amount of the light emitting element 16 is $-5,000$ ppm/°C., therefore, the temperature coefficient ($\partial Vo/\partial T$) of the output voltage Vo of the light receiving circuit can be made zero, and it is possible to render the temperature coefficient of the whole circuit to be eventually zero by setting the temperature coefficient of the driving current I6 in the driving circuit 17 for the light emitting element 16 to be 1,250 ppm/°C.

In the above formula (2), the resistor R7 is to be formed by a discrete part having a temperature coefficient which is negligible, and it is set that $V_{ZD3} = 6.9$ V, $\partial V_{ZD3}/\partial T = 3mV/°C.$, $\partial V_F/\partial T = -2mV/°C.$, and $V_F = 0.7$ V, then it is sufficient to render the value $$\{1/(6.9 - n \times 0.7)\} \cdot (3 \times 10^{-3} + n \times 2 \times 10^{-3})$$

to be 1,250 ppm/°C. $= 1.25 \times 10^{-3}$, upon which $n = 1.956 \approx 2$. Accordingly, the number of the diode may be made to be $(n-1) = 1$.

Carrying out optimumly in the foregoing manner the setting of the number of the (n−1) diodes in the driving circuit 17, it is possible to render the temperature coefficient of the output voltage of the light detection circuit to be zero.

Figure 8:
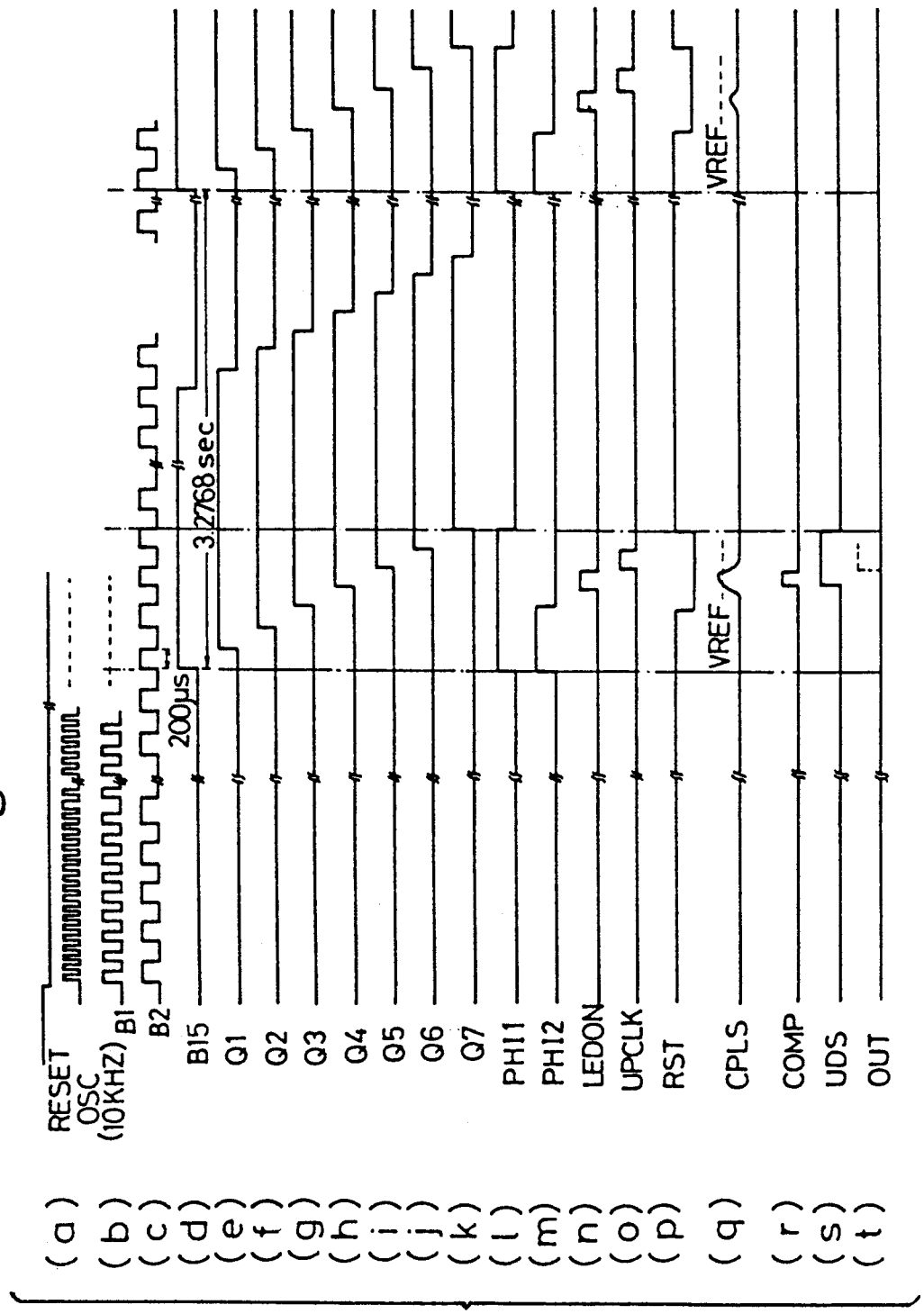
FIG. 8 shows waveforms at various parts in the sensor of FIG. 1.

Referring to FIG. 8, there is shown a time chart of an operation of the sensor according to the present invention, along the operation at respective parts of the sensor. When the reference clock signal OSC from the oscillation circuit 19 is of a frequency of 10 KHz (waveforms (a) and (b) in FIG. 8), the frequency divided output B15 of the 15 stage frequency divider 20a (waveform (d) in FIG. 8) will be a clock having a cycle of 3.276 sec. This frequency divided output B15 is provided to the 7 stage shift register circuit 20b, which circuit is made to shift by means of the second stage frequency divided output B2 of the frequency dividing circuit 20a (waveform (c) of FIG. 8), and thus the outputs Q1 through Q7 of the respective stages of the shift register circuit 20b (waveforms (e) to (k) of FIG. 8) are prepared. Signals of these outputs are decoded at the logical circuit 20c, and the control signals PHI1 and PHI2, light emission control signal LEDON, up-clock signals UPCLK and reset signal RST are prepared (waveforms (1) to (P) of FIG. 8). The control signal PHI1 is to render the analog signal processing circuit 21 including the amplifier 21a, reference voltage source 21b and comparator 21c to be effective and, for a period of time in which this control signal PHI1 is at L level, the source current to the analog signal processing circuit 21 is interrupted so as to be able to reduce the required consumption of the electric current. At the same time, the other control signal PHI2 rises to turn the analog switch SW1 ON, the buffer side terminal of the DC cutting capacitor C3 is charged by the reference voltage Vo, and a voltage equal to the reference voltage Vo is attained across the capacitor C3.

Figure 9:
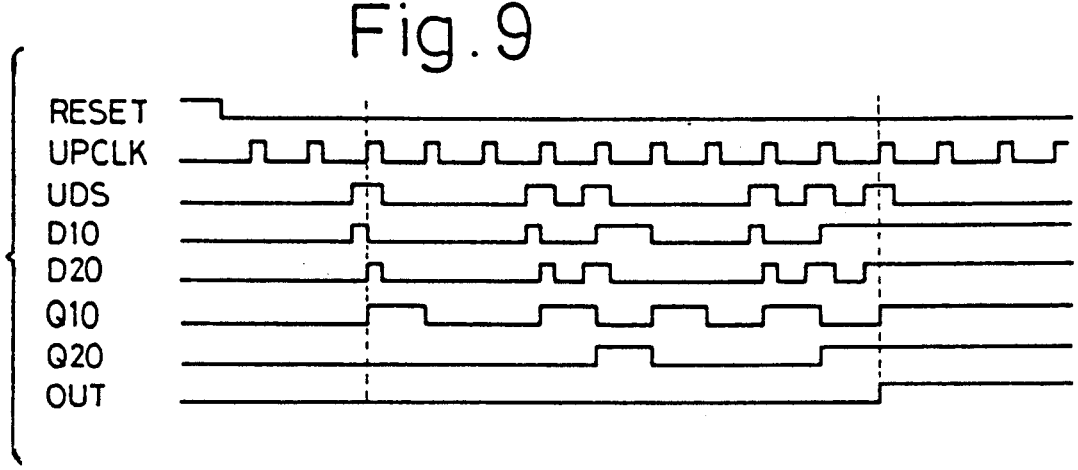
FIG. 9 shows operational waveforms of the counter circuit in the sensor of FIG. 1.
Figure 10:
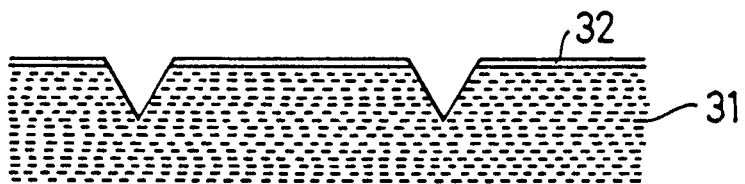
FIGS. 10 through 13 show in sectioned views a fabricating sequence of a dielectric isolation type integrated circuit realizing the sensor of FIG. 1.
Figure 11:
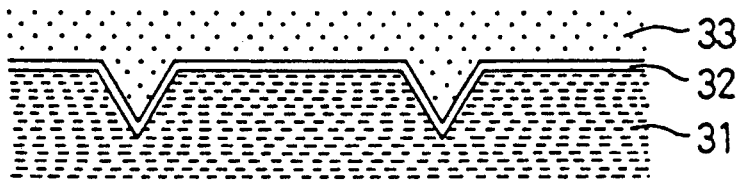
Figure 12:
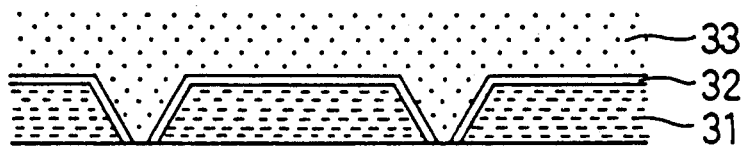
Figure 13:
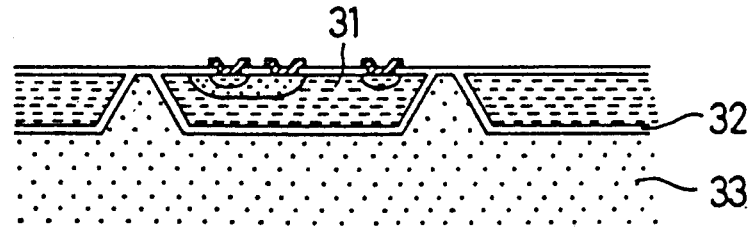

When on the other hand the control signal PHI2 is at L level and the analog switch SW1 is thereby turned OFF, the light emission control signal LEDON becomes at H level, and the driving current I6 is made to flow to the light emitting element 16 by the driving circuit 17. During this L level of the light emission control signal LEDON, the consuming current of the driving circuit 17 is also made zero. The output signal of the light receiving element 18 as obtained with the detection signal of the emitted light from the light emitting element 16 is amplified at the amplifier 21a and, as the received-light signal CPLS (waveform (q) of FIG. 8) exceeds the reference voltage $V_{REF}$ of the comparactor 21c, the comparison output signal COMP of the comparator 21c (waveform (r) of FIG. 8) will be at H level. This comparison output signal COMP is subjected to the self-holding by the RS flip-flop 15a in the counter circuit 15 and, when the up-down selection signal UDS (waveform (s) of FIG. 8) is at H level, the signal COMP is to be taken into the up-down counter 15b in the counter circuit 15 by means of the up-clock signal UPCLK. At the counter circuit 15, the sequential excess for three times of the received-light signal CPLS over the reference voltage $V_{REF}$ will cause an output signal OUT of the counter circuit 15 to be at H level (see also FIG. 9). The number of times for which the received-light signal CPLS and the reference signal $V_{REF}$ are compared with each other can be increased or decreased by properly setting the counter circuit 15.

A larger number of the sensors of the kind referred to are generally disposed as mutually separated between the circuit lines 11 and 12, and it is desirable to reduce the consuming power. In the foregoing analog signal processing circuit 21, too, it is attempted to save the consuming power of the analog signal processing circuit 21. In the present instance, the analog signal processing circuit 21 is actuated intermittently by the control signal PHI1 generated at the timing control circuit 20, so as to save the power. Assuming here that the source voltages Vc and Vd are 10 V and 5 V, respectively, and the H level period of the control signal PHI1 which renders the analog signal processing circuit 21 to be effective is 1.4 msec., then a current consumption of 10 mA practically required for the entire analog signal processing circuit 21 here should only result in the presence of the power consuming period for 1.4 msec. just once in a cycle of about 3.2 sec. so that $10mA \times 1.4$-$msec./3.2sec.=4.38$ µA, achieving a remarkable saving of the required power consumption. Further, no current flows through the driving circuit 17 at all so long as the light emission control signal LEDON is at L level. Even when the driving current I6 for the light emitting element 16 is to be 100 mA, therefore, with the H level period of the light emission control signal LEDON set to be 200 µsec., it is then attainable that $100mA \times 200$-$\mu sec./3.2sec.=6.25$ µA, and there can be attained a remarkable power saving.

In addition, there is a further power consumption of about 7 µA at the constant voltage circuit 21b and power-on reset circuit 22 but, since the logical circuit part including the timing control circuit 20 and counter circuit 15 is of less power consumption, the entire power consumption should be limited within 10 µA even when the oscillation circuit 19 of 10 KHz is included. Therefore, the power consumption in the sum total will be $$4.38+6.25+7+10=27.63(\mu A)$$

and thus the sensor as a whole is of a low power consumption of less than 30 µA. In the foregoing embodiment, further, the consumed power saving is attempted not by connecting and disconnecting the power source of the source lines Vc and Vd in intermettently driving such analog circuit parts as the driving circuit 17, analog signal processing circuit 21 and the like, but rather by interrupting the current with the transistors provided discretely for controlling the current interruption with respect to the respective analog circuit parts, so that required time for the respective analog circuit parts to reach effective state will be shorter than in the case where the source line voltage is connected and disconnected and consequently it will be made possible to have the received light output of the light receiving element 18 taken up at the counter circuit 15 within such a short period of time as 1.4 msec. as a whole. Accordingly, the effective operation time at the analog circuit parts is thereby made shorter and an attempt to save the consumed power can be attained.

According to one of remarkable features of the present invention, main circuit parts forming the sensor in the foregoing embodiment are provided as a semiconductor integrated circuit formed on a dielectric isolation substrate. Referring now to FIGS. 10 to 13, an N⁻ type single crystal silicon substrate 31 is subjected to a known semiconductor processing to have an insulating film 32 of an oxide ($SiO_2$) formed thereon, desired portions of this oxide film 32 are etched through photolithographic and oxide-film etching techniques, thereafter an anisotropic etching is carried out with respect to the silicon crystal by means of an alkaline anisotropic etching liquid, and V-shaped grooves are thereby formed (see FIG. 10). Thereafter, the isulating film 32 is also formed on surfaces of the grooves. Since this film 32 is for insulating purpose, it may not be limited only to $SiO_2$ but $Si_3N_4$ or the like may commonly be utilized. Next, a polycrystalline silicon layer 33 is formed as a supporter on the insulating film 32 (see FIG. 11). While not specifically limited, this polycrystalline silicon layer 33 should preferably be of a thickness substantially equal to that of the single crystal silicon substrate. Surface grinding is then carried out from the side of the silicon substrate 31 to remove the substrate until the insulating film 32 and polycrystalline silicon layer 33 at bottom portions of the etched grooves are exposed (see FIG. 12). The grinding is started with a coarse lapping and is continued with gradually finer lapping, and finally a polishing is carried out for a mirror finishing.

Through the foregoing steps, the dielectric isolation substrate including a plurality of single crystal silicon zones enclosed by the insulating film 32 and disposed in the form of many lands on the polycrystalline silicon layer 33 is completed. On the respective land-like single crystal silicon zones 31, such constituent members of the sensor circuit as has been disclosed, that is, the sensor elements to be provided in the IC formation are formed. In the foregoing sensor circuit, the elements which cannot be provided in the IC formation will be the power-source capacitors C1 and C2, light emitting element 16 and the high withstand voltage and high resistance value resistor R3 in the constant voltage circuit 13, and all other circuit elements than these can be formed into one-chip integrated circuits, with the effective minimization in size and weight simultaneously achieved. The resistor R3 of the high withstand voltage and high resistance value may be included in the one chip, so long as it is not problem that occupying area of the elements becomes larger.

According to the present invention, further, a variety of design modification is possible.

Figure 14:
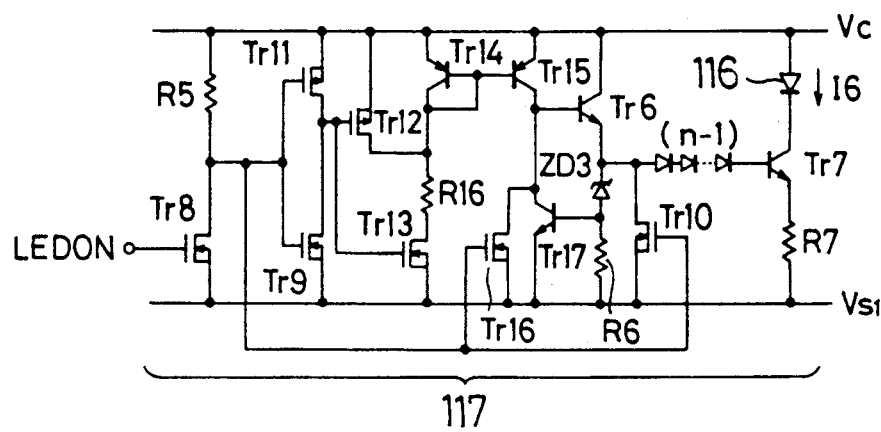
FIG. 14 is a detailed circuit diagram showing another working aspect of the light emitting element and its driving circuit which are employable in the sensor of FIG. 1.

Referring to FIG. 14, another working aspect of the driving circuit for the sensor according to the present invention is shown. In the present instance, the driving circuit 117 differs from the driving circuit 17 of FIG. 3 in respect that a current mirror circuit comprising PNP transistors Tr14 and Tr15 is added to achieve a constant current as the base current source for the transistor Tr6, and that the voltage $V_{BE7}$ across the base and emitter of the transistor TR7 is cancelled by a voltage $V_{BE17}$ across the base and emitter of a transistor Tr17 so that the temperature characteristics of the driving current I6 for the light emitting element 116 will be determined only by the Zener diode ZD3 and (n−1) diodes. All other arrangements are the same as those in the driving circuit 17 of FIG. 3 and the same constituent elements as those in the circuit 17 of FIG. 3 are denoted by the same reference numerals.

In the present instance, the light emission control signal LEDON at H level renders, as has been referred to with reference to FIG. 3, the NMOS transistor Tr8 to be turned ON, the NMOS transistors Tr9 and Tr10 turned OFF and the PMOS transistor Tr11 turned ON, whereby the gate potential is raised at the PMOS transistor Tr12 and NMOS transistor Tr13, so as to turn the PMOS transistor Tr12 to be OFF and the NMOS transistor Tr13 to be ON. Consequently, a constant current determined by the resistor R16 is made to flow to the PNP transistor Tr14 and an identical current is also made to flow through the PNP transistor Tr15 to the base of the transistor Tr6. The gate potential at the NMOS transistor Tr16 is low at this moment, and this transistor Tr16 is turned OFF and the NPN transistor Tr17 is placed to be ready to operate. This NPN transistor Tr17 is to carry out a negative feedback control in such that, as the voltage across the resistor R6 rises, the base current of the NPN transistor Tr6 is shunted to lower the voltage across the resistor R6 so as to be equal to the voltage $V_{BE17}$ across the base and emitter of the NPN transistor Tr17. Consequently, the driving current I6 for the light emitting element 116 in the driving circuit 117 will be $$I6 = \{(V_{ZD3} - (n-1) \cdot V_F\}/R7$$

This is due to that the voltage $V_{BE7}$ across the base and emitter of the transistor Tr7 and the voltage $V_{BE17}$ across the base and emitter of the transistor Tr17 are to cancel each other. Next, the light emission control signal LEDON at L level renders the NMOS transistor Tr8 to be turned OFF, NMOS transistors Tr9 and Tr10 to be ON and the PMOS transistor Tr11 to be OFF, so that the gate potential of the PMOS transistor Tr12 and NMOS transistor Tr13 is lowered to turn the PMOS transistor Tr12 to be ON and the NMOS transistor Tr13 to be OFF. Accordingly, no current is made to flow to the PNP transistor Tr14, nor to the PNP transistor 15. As the NMOS transistors Tr16 and Tr10 are turned ON, the base potential of the NPN transistors Tr6 and Tr7 is thereby lowered, and the both NPN transistors Tr6 and Tr7 come into complete OFF state. Therefore, the L level of the control signal PHI1 causes no current to flow from the source line Vc to the other source line $V_{S1}$ at all.

Now, the number of the (n−1) diodes employed in the driving circuit 117 is to be set so that the temperature coefficient on the light emitting side and light receiving side will be zero as a whole, taking into consideration the temperature coefficient of the Zener voltage $V_{ZD3}$ of the Zener diode ZD3, light emission efficiency of the light emitting element 116, light receiving efficiency of the light receiving element and the temperature coefficient of the high resistor R8 for the current-voltage conversion. In the concrete, the driving current I6 to the light emitting element 116 will be $$I6 = \{V_{ZD3} + V_{BE} - (n-1)V_F - V_{BE}\}/R7 = \{V_{ZD3} - (n-1)V_F\}/R7$$

The same calculation carried out as in the foregoing results in n=3, and the number of the diodes should be (n−1)=2. Therefore, the light-emission driving circuit of a constant temperature coefficient for the output voltage can be thus realized.

Figure 15:
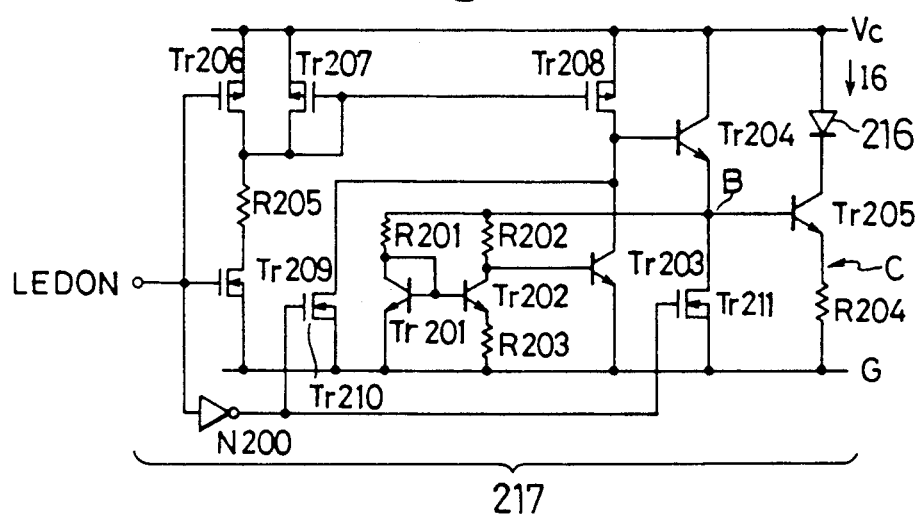
FIG. 15 is also a detailed circuit diagram showing still another working aspect of the light emitting element and its driving circuit employable in the sensor of FIG. 1.

Referring to FIG. 15, there is shown still another embodiment of the driving circuit adapted to the sensor in the IC formation according to the present invention, and it is also intended to render the temperature fluctuation component to be zero in the driving circuit 217 of this embodiment. More specifically, the light emission signal S is applied in the present instance to the gates of PMOS transistor Tr206 and NMOS transistor Tr209, and the logical value inverted by an inverter N200 is provided to the gates of the NMOS transistors Tr210 and Tr211. As the light emission signal S becomes H level, therefore, the PMOS transistor Tr206 is turned OFF while the NMOS transistor Tr209 is turned ON, whereby a current mirror circuit formed by PMOS transistors Tr207 and Tr208, NMOS transistor Tr209 and resistor R205 is actuated. The output of the inverter N200 becomes L level, and the NMOS transistors Tr10 and Tr11 are turned OFF. Therefore, a band cap reference circuit formed by NPN transistors Tr201, Tr202, Tr203 and Tr204 and resistors R201, R202 and R203 receives a supply of a current.

A voltage $V_B$ represented by a following formula is thereby generated at point B in the driving circuit 217 of FIG. 15:

$$V_B = V_{BE3} + V_T\{(R202/R203) \cdot ln \cdot (R202/R201)\} \quad (3)$$

wherein $V_{BE3}$ is the normal directional voltage across the base and emitter of the transistor Tr203, and $V_T$ is to be represented by a following formula, with k representing the Boltzmann's constant, representing the electron charge and T representing the absolute temperature, $$V_T = kt/q \quad (4)$$

Here, as the NPN transistor Tr205 is operating in non-saturating state, there is generated at point C, with a voltage across the base and emitter of this transistor assumed to be $V_{BE205}$, such a voltage as represented by $$V_C = V_B - V_{BE205}$$

so that a constant current represented by $$I6 = V_C/R204 = (V_B - V_{BE205})/R4 \quad (5)$$

will flow through the light emitting element 216.

As the light emission signal S becomes L level here, the transistor Tr206 is turned ON while the transistor Tr209 is turned OFF so as not to cause any current to flow to the current mirror circuit formed by the transistors Tr207, Tr208 and Tr209 and the resistor R205, and the transistors Tr210 and Tr211 are turned ON to render no base current to flow to the transistors Tr205 and Tr206 so as to turn them OFF, so that no current will flow to the light emitting element 216.

Assuming now that a photoelectric current I8 is generated at such light receiving element 218 with light irradiated thereon, a variation component $v_o$ in the output Vo of this element will be $$v_o = I8 \cdot R206 \quad (6)$$

In this case, the input impedance of the operational amplifier 221a is very high, and the photoelectric current I8 in the light receiving element 218 is caused to flow all through the feedback resistor R206, and the above formula (6) is satisfied. To the operational amplifier 221a, the output from the reference voltage source 221b is being provided.

From the above formula (6), the temperature fluctuation component of $v_o$ will be $$(1/v_o) \cdot (\partial v_o / \partial T) = (1/I8) \cdot (\partial I8/\partial T) + (1/R206) \cdot (\partial R206/\partial T) \quad (7)$$

Assuming here that the light receiving element 218 is a photodiode, the resistor R206 comprises a diffusion resistor in IC formation and their temperature fluctuation components $(1/I8) \cdot (\partial I8/\partial T)$ and (1/R206)·(∂R206/∂T) are 3,000 ppm/°C. and 3,700 ppm/°C., respectively, then the temperature fluctuation component (1/v$_o$)·(∂v$_o$/∂T) of the output voltage v$_o$ will be 6,700 ppm/°C. In an event where the light emitting element 216 shown in FIG. 15 is made to be a generally employed light emitting diode (LED) and the entire temperature fluctuation component is attempted to be zero, it may be sufficient to render the temperature fluctuation component of the driving current I6 of the driving circuit 217 for the light emitting element 216 to be 3,300 ppm/°C.

The driving current I6 can be represented by the formula (5), its temperature fluctuation component will be $$(1/I6) \cdot (\partial I6/\partial T) = \{(\partial V_B/\partial T) - (\partial V_{BE206}/\partial T)\}/(V_B - V_{BE206})] - (1/R204) \cdot (\partial R204/\partial T) \quad (8)$$

From the foregoing formula (3), further, the temperature coefficient of the B point voltage will be $$(\partial V_B/\partial T) = (\partial V_{BE203}/\partial T) + (\partial V_T/\partial T) \cdot (R205/R203) \cdot \ln \cdot (R202/R201) \quad (9)$$

Assuming here that the resistor R204 is a discrete part of a negligible temperature fluctuation and setting $V_{BE203} = V_{BE206} = 0.7 V$, $\partial V_{BE203}/\partial T = \partial V_{BE206}/\partial T = -2 mV/°C.$, $\partial V_T/\partial T = 0.085 mV/°C.$ and the value of the respective resistors R201 to R203 to be R201=3 KΩ, R204=30 KΩ and R205=1 KΩ, then, from the foregoing formula (3), V$_B$=2.5 V. From the above formula (9), $$\partial V_B/\partial T = -2mV/°C. + 5.87mV/°C. = 3.87mV/°C. \quad (10)$$

Substituting the above formulas (10) and (11) by the foregoing formula (8), $$(1/I6) \cdot (\partial I6/\partial T) = \{3.87 \text{ mV/°C.} - (-2 \text{ mV/°C.})\}/(2.5 - 0.7) - 0$$
$$\approx 3,300 \text{ ppm/°C.}$$

Figure 16:
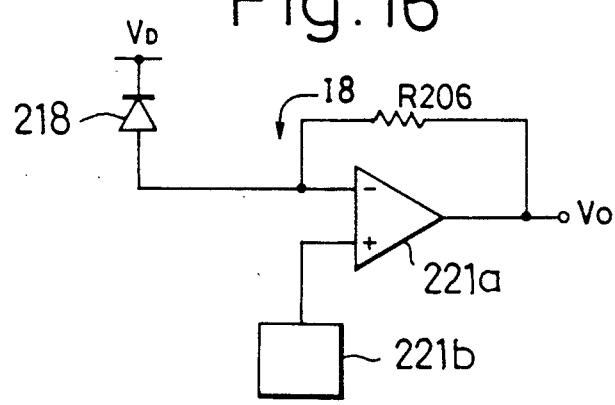
FIG. 16 is a circuit diagram showing a light receiving element employable in combination with the light emitting element of FIG. 15.

It may be appreciated from the above that the temperature fluctuation component of such related circuits as shown in FIGS. 15 and 16 of the light emitting and receiving elements 216 and 218 can be made zero by optimumly setting the value of the resistors R201–R203.

Referring now to FIG. 17 in which another working aspect of the analog signal processing circuit applicable to the sensor in IC formation according to the present invention is shown, the circuit 421 is more simplified in the structure than in the case of the circuit 21 shown in FIG. 4 and the adaptability of the circuit to the one chip formation is thereby elevated. In FIG. 17, elements corresponding to those in FIG. 4 are denoted by the same reference numerals as those in FIG. 4 but as added by 400. Referring more specifically, the analog signal processing circuit 421 in the present embodiment comprises three stage operational amplifiers OP401–OP403, capacitors C401 and C403 connected respectively across an output terminal and an inverted input terminal of the operational amplifiers OP401 and OP403, and a bilateral switching element SW401 connected to the operational amplifier OP403 in parallel with the capacitor C403. Referring also to FIG. 18, a gate signal SW at H level causes the switching element SW401 turned ON, and the output voltage of the operational amplifier OP403 is set to be the reference voltage V$_{ref}$. The gate signal SW is held at H level for a predetermined period of time and is thereafter made to be L level. In the comparator 421c, JFET or MOS transistor of a high input impedance is employed as an input stage transistor, an input bypassing current of which is extremely small as to be several pA to about 100 pA. Therefore, the output terminal voltage of the operational amplifier OP403 is held substantially at the reference voltage V$_{ref}$ for several msec. after turning OFF of the switching element SW401, even if the capacity of the capacitors C402 and C403 is so small as to be about 10 pF. As the gate signal SW rises and the oscillation signal of the oscillation circuit causes the light emitting element 416 to emit light, the amplifying means 421a of the analog signal processing circuit generates an output signal Vs, upon which the switching element SW401 is in OFF state and the operational amplifier OP403 operates as an inverting amplifier of a gain of −(jwC403/jwC402). If, for example, C402=C403, the output signal of the amplifying means 421a involving even an error voltage of ΔV generated in the sense of direct current renders an inverted output signal of the output signal of the operational amplifier OP403 as the inverting amplifier. If the variation of this input voltage is more than a predetermined value, the comparator 421c provides a detection signal. In the present embodiment, the reference voltage provided to the non-inverted input terminal of the operational amplifier OP403 as the inverting amplifier may be different from the reference voltage V$_{ref}$ which is provided to the amplifying means 421a.

Figure 20:
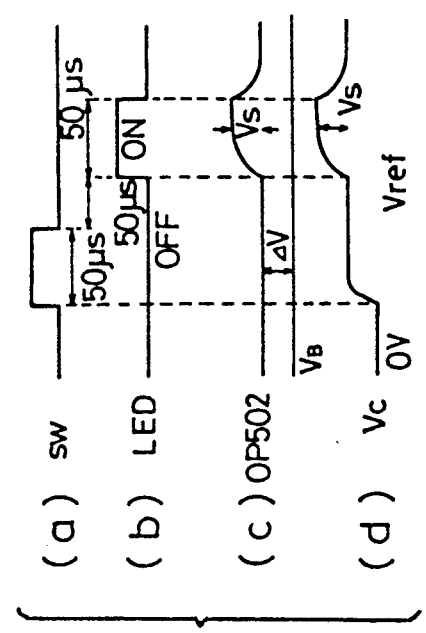
FIG. 20 shows operational waveforms in the circuit of FIG. 19.

According to another feature of the present invention, there is suggested an arrangement allowing even a faint input signal to be accurately detected. Referring here to FIG. 19, there is inserted a DC cutting circuit between the amplifying means 521a and the comparator 521c, and a CMOS transistor Tr501 comprising NMOS transistor Tr501a and PMOS transistor Tr501b is connected between the output terminal of the capacitor 502 and the reference voltage source V$_{ref}$. The NMOS transistor Tr501a can be made ON and OFF by means of the gate signal SW while the PMOS transistor Tr501b is turned ON and OFF by an inverted signal of the gate signal SW through an inverter N500. The reference voltage V$_{ref}$ may be a ground voltage (zero voltage). Accordingly, referring also to FIG. 20, the gate signal SW reaching H level causes the NMOS transistor Tr501a and PMOS transistor Tr501b to be turned ON, and the voltage V$_C$ at the output terminal of the capacitor C502 is set at the reference voltage. The gate signal SW is held at H level for about 50 μsec. and is thereafter made to be L level. The comparator 521c is substantially of the same structure as the comparator 421c of FIG. 17, the input bypassing current is so small as to be about several pA to 100 pA and is held at the reference voltage V$_{ref}$ for several msec. even when the capacity of the capacitor C502 is small, and a detection signal is provided in response to a component of the output signal Vs in the same manner as in the embodiment of FIG. 17. In this case, the output terminal voltage of the capacitor C502 is set at the reference voltage V$_{ref}$ in accordance with the gate signal SW prior to the detection period of the input signal, even when the output of the operational amplifier OP502 involves the error signal ΔV due to an off-set voltage of the operational amplifiers OP501 and OP502 and a dark current of the light receiving element 518, and the error signal ΔV is not provided to the comparator 521c. Accordingly, it is made possible to accurately detect only the faint input signal.

Figure 21:
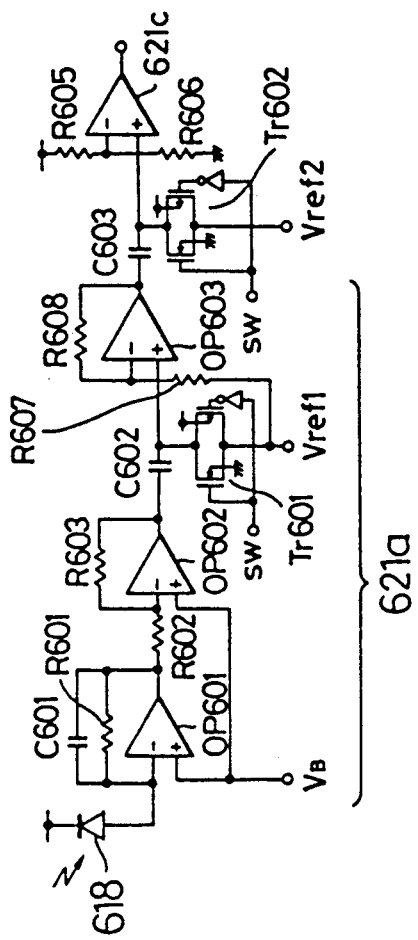
FIG. 21 shows the light receiving element and signal processing circuit in yet another working aspect employable in the sensor of FIG. 1.

Referring next to FIG. 21, there is suggested an amplifying arrangement which is more improved in the detecting function of the faint current than the analog signal processing circuit of FIG. 17. That is, in the present instance, three stage operational amplifiers OP601, OP602 and OP603 are provided in the same manner as in the amplifier of FIG. 4, and CMOS transistors Tr601 and Tr602 forming the same DC cutting circuit as that shown in FIG. 17 are inserted between the output terminal of the second operational amplifier OP602 and the input terminal of the third operational amplifier OP603 and between the first operational amplifier OP603 and the comparator 621c, respectively, so that the DC cutting circuit inserted between the second and third operational amplifiers OP602 and OP603 will be effective to prevent the error voltage ΔV generated by the output of the second operational amplifier OP602 from being amplified by the third operational amplifier OP603. While the amplification factor can be thus increased, the amplification of any error can be avoided so that the sensing function of the sensor can be remakably increased.

Figure 23:
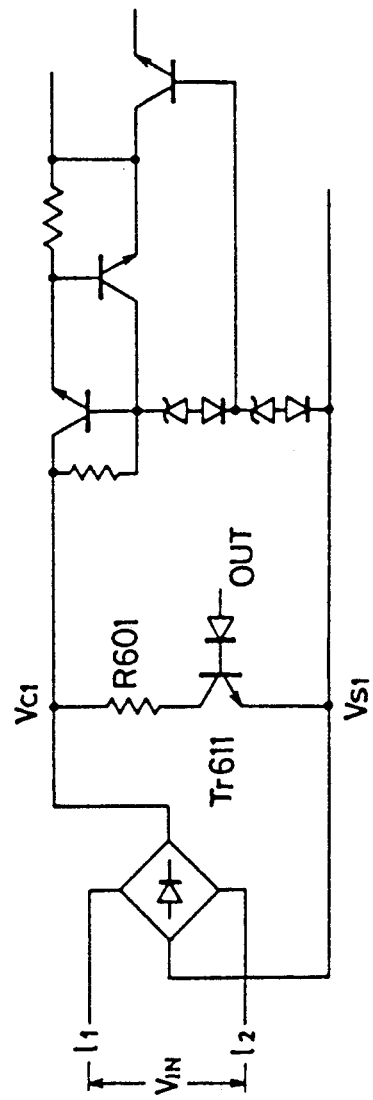
FIG. 23 is a detailed fragmentary circuit diagram in another working aspect of the sensor in which the counter circuit of FIG. 22 is employed.
Figure 22:
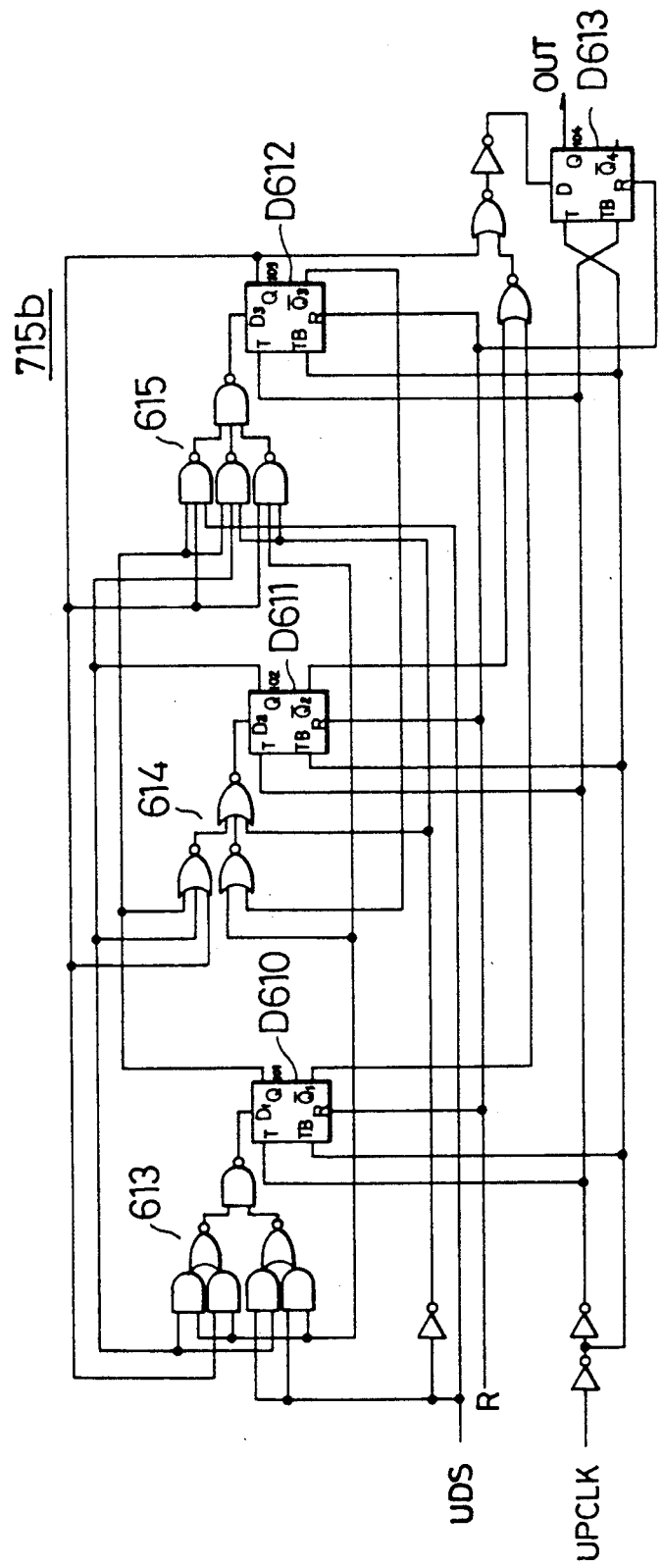
FIG. 22 is a detailed circuit diagram in another working aspect of the counter circuit employable in the sensor of FIG. 1.

According to still another feature of the present invention, the up-down counter is provided with an automatic resetting function. Referring to FIG. 22, another working aspect of the up-down counter 715b shown therein comprises four D flip-flops D610–D613 and three logical circuits 613–615. In the present instance, the function of providing the trigger signal for short-circuiting the sensor circuit lines 11 and 12 upon presence of three sequential H level outputs of the analog signal processing circuit is the same as the up-down counter 15b in FIG. 5. Instead of such thyristor employed as the switching element as in FIG. 5, however, NPN transistor Tr611 and resistor R611 are employed as shown in FIG. 23 so that, even when the output signal OUT of the up-down counter 715b is at H level, the voltage across the source lines $V_{C1}$ and $V_{S1}$ will be maintained at a voltage corresponding to a difference between the voltage across the lines 11 and 12 and the voltage fall $2V_D$ at the diode bridge, that is, $V_{IN} - 2V_D$, so as to have the circuit operation continued. In this case, a current flowing through the NPN transistor Tr611 causes the circuit current to be increased, the receiver connected between the circuit lines 11 and 12 detects this increased circuit current and an alarm signal is to be thereby generated. Therefore, the output signal OUT of the up-down counter 715b of FIG. 22 is made to be at L level when the detection input disappears, the NPN transistor Tr611 is turned OFF in response thereto and the circuit is to be automatically reset.

What is claimed is:

1. A sensor in an IC formation, which comprises sensor circuit lines connected to a switching means for short-circuiting between the lines and a power source means for taking a power source voltage out of the lines, the power source means being connected at its post stage to an intermittent operating means, light emitting means and driving means for said light emitting means, the intermittent operating means being arranged to intermittently actuate the light emitting means, a light receiving means disposed for receiving a faint pulsed light generated by scattering of light emitted from said light emitting means, a comparing means of signals received as amplified from said light receiving means together with a reference signal, and a counter means for providing a trigger signal to said switching means in response to an output signal from said comparison means, wherein constituent elements of respective said means are in said IC formation and formed as integrated circuits on a dielectric isolation substrate.

2. A sensor according to claim 1 wherein said constituent elements formed as integrated circuits are all of the other elements constituting said switching, driving, intermittent operation, light emitting, light receiving, comparison and counter means, a light emitting element, driving means for said light emitting element, operating means arranged for driving said driving means to intermittently actuate said light emitting means; and a resistor of a high withstanding voltage and a high resistance value in a constant voltage circuit included in said intermittent operation means.

3. A sensor according to claim 2 wherein said resistor is also provided as said integrated circuit.

4. A sensor according to claim 1 which further comprises means for regulating temperature coefficient of a driving current of said driving means with respect to temperature coefficient of a light emitting element of said light emitting means.

5. A sensor according to claim 1 which further comprises means for rendering the sum total of a temperature coefficient of a received-light output current from said light receiving means and a temperature coefficient of a resistance value of a resistor means for converting said received-light output current into a voltage signal to be substantially zero.

6. A sensor according to claim 1 which further comprises first and second power supply lines connected to said circuit lines, said switching means being positioned in an electric path between said first and second power supply lines for being shifted into a low impedance state when a control signal generated at said intermittent operation means is of one of logical values thereof but into a high impedance state when said control signal is of the other logical value.

7. A sensor according to claim 1 which further comprises an amplifying means connected between said light receiving means and said comparison means, said amplifying means including an inverted amplification means; a first capacitor inserted between an inverted input terminal of said inverted amplification means and said light receiving means; and a parallel circuit of a switching element and second capacitor connected across said input terminal and an output terminal of the inverted amplification means, said switching element being made ON and OFF prior to said operation of the light emitting means.

8. A sensor according to claim 7 which further comprises a DC cutting transistor provided with respect to said inverted amplification means.

9. A sensor according to claim 7 wherein said amplifying means comprises a plurality of amplifying elements and a plurality of DC cutting transistors.

10. A sensor according to claim 1 wherein said counter means includes an up-down counter having an automatic resetting function.

* * * * *